(12) United States Patent
Johnson et al.

(10) Patent No.: US 11,990,213 B1
(45) Date of Patent: May 21, 2024

(54) METHODS AND SYSTEMS FOR VISUALIZING PATIENT POPULATION DATA

(71) Applicant: Allscripts Software, LLC, Raleigh, NC (US)

(72) Inventors: Mary Sumner Johnson, Raleigh, NC (US); Todd Michael Eischeid, Cary, NC (US); Ohad Young, Tel Aviv (IL); Ross Carlyle Teague, Cary, NC (US)

(73) Assignee: ALTERA DIGITAL HEALTH, Chicago, IL (US)

( * ) Notice: Subject to any disclaimer, the term of this patent is extended or adjusted under 35 U.S.C. 154(b) by 1020 days.

(21) Appl. No.: 15/265,815

(22) Filed: Sep. 14, 2016

(51) Int. Cl.
*G16H 10/60* (2018.01)
*G06F 16/248* (2019.01)
(Continued)

(52) U.S. Cl.
CPC ........... *G16H 10/60* (2018.01); *G06F 16/248* (2019.01); *G06F 16/9535* (2019.01);
(Continued)

(58) Field of Classification Search
CPC ........ G06Q 50/22; G06Q 10/10; G06Q 50/24; G06Q 10/06; G06Q 10/103; G06Q 10/107; G06Q 10/109; G06Q 2220/00; G06Q 40/02; G06Q 10/00; G06Q 30/02; G06Q 30/0603; G06Q 40/04; G16H 10/60; G16H 10/20; G16H 15/00; G16H 40/63; G16H 50/20; G16H 10/65; G16H 20/17; G16H 40/20; G16H 50/30; G16H 50/50; G16H 80/00; G16H 50/70; G16H 10/40; G16H 10/00; G16H 40/40; G16H 40/67; G16H 70/00; G16H 70/20; G06F 19/00; G06F 19/3456; G06F 19/3468; G06F 19/324; G06F 19/3418; G06F 19/3462; G06F 19/3475; G06F 19/3481; G06F 3/0482; G06F 3/04842; G06F 3/04847; G06F 19/32; G06F 19/321; G06F 19/322; G06F 19/36; G06F 21/6245; G06F 3/04817; G06F 16/958; G06F 19/328; G06F 21/6254; G06F 19/325; G06F 21/6263; G06F 16/83; G06F 16/9535; G06F 19/326; G06F 21/602; G06F 21/604; G06F 21/6227; G06F 2221/2107; G06F 16/951; G06F 16/248; A61B 2560/0276; A61B 2560/0456; A61B 5/002; A61B 5/0022; A61B 5/0205;
(Continued)

(56) References Cited

U.S. PATENT DOCUMENTS 8,521,565 B2   8/2013   Faulkner et al.
8,650,045 B2   2/2014   Baldock et al.
(Continued)

*Primary Examiner* — Lynda Jasmin
*Assistant Examiner* — Kimberly L Evans
(74) *Attorney, Agent, or Firm* — Calfee, Halter & Griswold LLP

(57) ABSTRACT

Technologies pertaining to assigning patients to patient populations and graphically indicating that the patients have been assigned to the patient populations are described herein. A graphical user interface includes interactive elements that are configured to indicate to a healthcare worker (Continued)

that a patient has been assigned to a population, and further to depict proposed actions based upon the patient being assigned to the population.

19 Claims, 6 Drawing Sheets

(51) Int. Cl.
*G06F 16/9535* (2019.01)
*G16H 40/63* (2018.01)
*G16H 50/30* (2018.01)
*G16H 70/20* (2018.01)

(52) U.S. Cl.
CPC ............. *G16H 40/63* (2018.01); *G16H 50/30* (2018.01); *G16H 70/20* (2018.01)

(58) Field of Classification Search
CPC ..... A61B 5/021; A61B 5/024; A61B 5/02438; A61B 5/04012; A61B 5/0402; A61B 5/0424; A61B 5/0816; A61B 5/14551; A61B 5/6843; A61B 5/6887; A61B 5/7275; A61B 5/742; A61B 5/746; A61B 5/7475; A61B 5/0002; A61B 6/566; A61B 8/565; A61M 2202/07; A61M 2205/35; A61M 5/14244; Y10S 707/99943; Y10S 901/01; Y10S 901/03; Y10S 901/47; B25J 11/009; B25J 9/163; B25J 9/1674; H04L 63/0428; H04L 67/02; H04L 63/20; H04L 67/00; H04L 67/12; H04L 69/329; H04L 67/10; H04L 67/26; H04L 67/30; H04L 29/06; H04L 63/105; H04L 67/2838; H04L 67/2871; H04L 2463/102; H04L 63/0823; H04L 63/102; H04L 63/1441; H04L 67/16; H04L 67/2819; H04L 67/2842; H04L 67/42; Y02P 90/84; Y02A 90/22; Y02A 90/26; G06T 11/206; H04W 4/206; H04W 4/21

USPC .................................. 705/1.1, 2, 3; 700/253
See application file for complete search history.

(56) References Cited

U.S. PATENT DOCUMENTS

| | | | |
|---|---|---|---|
| 9,760,962 B2 * | 9/2017 | Lese | G06Q 50/24 705/2 |
| 10,642,445 B2 * | 5/2020 | Quinn | G06F 3/0482 705/2 |
| 2008/0195420 A1 * | 8/2008 | Ramelson | G16H 10/60 705/3 |
| 2012/0150564 A1 | 6/2012 | Lese | |
| 2012/0215560 A1 * | 8/2012 | Ofek | G16H 70/20 705/3 |
| 2013/0332194 A1 * | 12/2013 | D'Auria | G16H 10/60 705/3 |
| 2014/0136234 A1 * | 5/2014 | Weinstein | G06F 19/00 705/3 |
| 2015/0019259 A1 * | 1/2015 | Qureshi | G16H 40/20 705/3 |
| 2015/0112710 A1 * | 4/2015 | Haber | G06F 19/3431 705/2 |
| 2015/0242571 A1 * | 8/2015 | Naeymi-Rad | G16H 10/60 705/3 |
| 2015/0324089 A1 | 11/2015 | Dart et al. | |
| 2015/0363568 A1 * | 12/2015 | Milo | G06F 19/3431 705/2 |
| 2016/0004820 A1 * | 1/2016 | Moore | G16H 15/00 705/3 |
| 2016/0055300 A1 * | 2/2016 | Ganesh | G16H 10/60 705/3 |
| 2016/0217254 A1 | 7/2016 | Douglass | |
| 2016/0250751 A1 | 9/2016 | Martinson et al. | |
| 2017/0124216 A1 * | 5/2017 | Miller | G16H 10/60 705/3 |
| 2017/0199987 A1 * | 7/2017 | Loeb | G06F 19/328 700/253 |
| 2020/0111578 A1 * | 4/2020 | Koblick | G16H 80/00 705/3 |

* cited by examiner

METHODS AND SYSTEMS FOR VISUALIZING PATIENT POPULATION DATA

BACKGROUND

Electronic health record systems (EHRs) are used by clinicians and others who provide medical services to facilitate interactions with patients, collection of patient data, presentation of patient data, billing, and a wide variety of other tasks related to the provision of healthcare. As the range of tasks that are completed using EHRs has grown, the volume of patient data managed by EHRs has increased. At the same time, clinicians in many healthcare environments are treating large numbers of patients. In order to provide care most efficiently, clinicians may seek to identify and prioritize treatment of patients of potentially highest risk for various ailments and other health conditions.

Currently, in order to assist clinicians in identifying and tracking patients of a potentially highest risk, conventional EHRs must 1) present patient health records of a plurality of patients to a clinician interacting with a client application of the EHR one at a time; 2) receive manual indications from the clinician for first patients in the plurality of patients having a first risk factor for a medical condition; 3) update a list of the first patients having the first risk factor responsive to receiving the manual indications of the first patients; 4) if patient risk is correlated with more than one risk factor, present patient health records of the first patients one at a time; 5) receive manual indications from the clinician by way of the EHR client application, the manual indications being for second patients in the list of the first patients; and 6) responsive to receiving the manual indications of the second patients, assign data indicative of the patient risk to the respective health records of the second patients. Conventional EHRs, then, require a clinician to manually examine perhaps hundreds of patient health records to identify potentially high-risk patients.

SUMMARY

The following is a brief summary of subject matter that is described in greater detail herein. This summary is not intended to be limiting as to the scope of the claims.

Described herein are various technologies pertaining to a computer-executable population health application, wherein the population health application is configured to improve the efficiency of identifying and treating patients based upon patient risk factors such as gaps in care or potential risk for disease. The population health application is a distributed application that includes population health client software executing on a client computing device in communication with population health server software executing on a server computing device. The population health application is configured to be used together with an electronic health record application (EHR). Like the population health application, the EHR application is a distributed application that includes EHR client software executing on a client computing device in communication with EHR server software executing on a server computing device. In an exemplary embodiment, a client computing device executes both the population health client software and the EHR client software, while first and second servers respectively execute the population health server software and the EHR server software. As will be described in greater detail herein, the population health application and the EHR are configured to act in conjunction to assign patients of a healthcare entity (where the EHR maintains patient records for patients of the healthcare entity) to health populations maintained by the population health application. Accordingly, users of these applications can quickly identify which patients are at risk of one or more medical conditions, can be presented with a list of patients at the healthcare facility that fall into a particular population, etc.

In a more detailed example, a client computing device executes the EHR client and the population health client. The EHR client receives an indication of a patient health record stored at a first server computing device that executes the EHR server, wherein the client computing device is operated by a user of the EHR (such as a clinician). The client computing device communicates a request for the patient health record to the first server computing device, whereupon the first server computing device transmits data to the client computing device that causes the client computing device to display data pertaining to the patient (e.g., the EHR client, when executed by the client computing device, causes the client computing device to display the data pertaining to the patient). The population health client is in communication with the EHR client, and causes the client computing device to communicate a request indicative of the patient to the second server computing device that executes the population health server. The population health server retrieves population health data pertaining to the patient from data stored at the second server computing device (or retrievable from the second server computing device), and the population health server computing device transmits information to the client computing device responsive to retrieving the population health data. For instance, this information can be or include data label that is indicative of one or more patient populations to which the patient belongs. The population health client, when executed by the client computing device, causes the client computing device to display such information to the operator of the client computing device. Hence, the EHR and the population health application act in conjunction to inform a clinician, at the point of care, that the patient has been labeled as belonging to one or more patient populations. For instance, the label can indicate that the patient belongs to a population of diabetics, thereby notifying the clinician that the clinician may wish to take steps to diagnose whether or not the patient has diabetes.

In another example, the EHR and the population health application can operate in conjunction to identify potential gaps in care and/or to identify patients where proactive care may be appropriate. As indicated above, the population health server can assign population labels to patients, where a population label indicates that the patient belongs to a particular population. Hence, a data structure maintained by the population health server (at the second server computing device) can include patient identifiers, population labels corresponding to the patient identifiers, and an indication that health records are maintained by the EHR. Accordingly, an operator of the client computing device can retrieve lists of patients that are assigned to one or more patient populations by the population health server. For instance, the user of the client computing device can interact with the client EHR to cause the client EHR to retrieve patient identifiers from the first server computing device (executing the server EHR) for some set of patients who receive care at the healthcare enterprise (e.g., the user can cause the client computing device to retrieve a list of patient identifiers of patients who have not had an office visit in the last calendar year). As indicated previously, the EHR client and the population health client can communicate with one another—accordingly, the operator of the client computing device can, via the population health client, transmit a query to the population health server, wherein the query includes the list of patient identifiers and a population of interest to the user. For instance, the population health client, when executed by the client computing device, can transmit a query to the second server computing device, where the query includes the list of patients and an identifier of a population (e.g., diabetes). The population health server, executing on the second server computing device, searches over the above-described data structure and retrieves search results, where the search results include a subset of the above-mentioned set of patients, and where each patient in the subset has been assigned to the population identified in the query (e.g., diabetes).

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
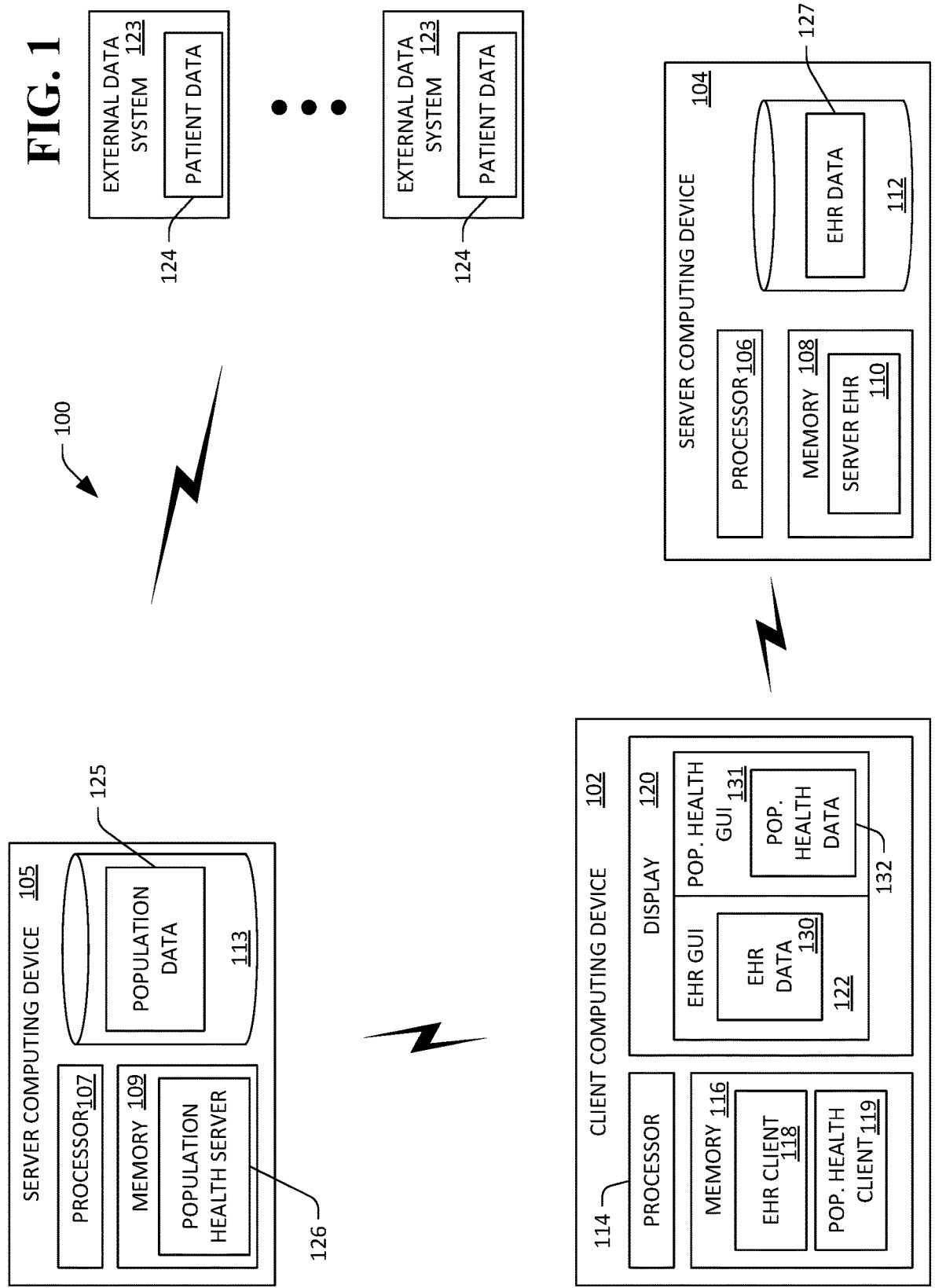
FIG. 1 is a functional block diagram of an exemplary computing system that is configured to cause patient population data to be presented on a display of a client computing device.

Various technologies pertaining to an electronic health record application (EHR) and a population health application that act in conjunction with one another are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Additionally, as used herein, the term "exemplary" is intended to mean serving as an illustration or example of something, and is not intended to indicate a preference.

Briefly, aspects described herein pertain to presenting data to a healthcare worker in a healthcare enterprise that indicates that at least one patient has been assigned to a particular patient population. With more detail, an EHR and a population health application can act in conjunction to present such data to the healthcare worker. Accordingly, a computing system described herein can cause a client computing device to present the healthcare worker with an indication that a certain patient has been assigned to a population at the point of care. In another example, the computing system described herein can cause the client computing device to present the healthcare worker with a list of patients that have been assigned to one or more patient populations, thereby allowing the healthcare worker to proactively address potential health issues of patients.

For sake of clarity, an EHR is a distributed application that includes EHR client software executing on a client computing device in communication with EHR server software executing on a server computing device. The EHR is configured to perform tasks related to a healthcare enterprise, including patient intake, maintenance of electronic records about patients of the healthcare enterprise, prescriptions, and the like. A population health application is a distributed application that includes population health client software executing on a client computing device in communication with population health server software executing on a server computing device. The population health application is configured to be used together with the EHR, and is generally configured to assign patients to patient populations. For instance, a patient population may be "diabetes", and the population health application can be configured to assign a patient to the patient population "diabetes" based upon data about the patient in an electronic record maintained by the EHR. The population health application can utilize any suitable approach for assigning a patient to a patient population, including a rules-based approach, clustering, and so forth. As used herein, the terms "EHR client" and "EHR server" refer to the EHR client software and EHR server software, respectively, while the terms "population health client" and "population health server" refer to population health client software and the population health server software, respectively. Various examples are set forth herein as to functionalities of the EHR and the population health application; however, it is to be understood that the EHR application can be configured to perform functionality described herein as being performed by the population health application.

With reference to FIG. 1, an exemplary system 100 is illustrated that improves upon existing computing systems used in healthcare environments by automatically identifying and presenting clinicians and other healthcare workers with information about patients most likely to be at risk for various medical conditions, or patients most in need of preventive care. The system 100 includes a client computing device 102 that is operated by a clinician or other healthcare worker (e.g., care managers, care navigators, etc.) in a healthcare environment. It is to be understood that while reference is made below to clinician interactions with the client computing device 102, other healthcare workers can interact with the client computing device 102 in embodiments described herein. The client computing device 102 may be any suitable type of computing device including, but not limited to, a laptop computing device, a tablet computing device, a mobile telephone, a kiosk, etc. The system 100 further includes a first server computing device 104 that is in network communication with the client computing device 102. For example, the first server computing device 104 and the client computing device 102 can be co-located in a healthcare facility. In another example, the first server computing device 104 may be remotely located from the client computing device 102 (e.g., the first server computing device 104 may be "in the cloud"). The system 100 further includes a second server computing device 105 in network communication with the client computing device 102 and the server computing device 104.

The first server computing device 104 includes a processor 106 and memory 108. The memory 108 has an EHR server 110 loaded therein, wherein the EHR server 110 is executed by the processor 106. The server computing device 104 also includes a data store 112 that stores data relating to healthcare workers, patients, etc. The second server computing device 105 includes a processor 107, memory 109, and a data store 113. The memory 109 of the second server computing device 105 has a population health server 126 loaded therein, such that the processor 107 executes the population health server 126.

The client computing device 102 includes a processor 114 and memory 116, wherein an EHR client 118 and a population health client 119 are loaded in the memory 116 and executed by the processor 114. The EHR client 118, when executed by the processor 114, is configured to be in communication with the EHR server 110 executing on the server computing device 104 and the population health client 119 executing on the client computing device 102. For instance, the EHR client 118 may be an application that is dedicated to the EHR 110. In another example, the EHR client 118 may be executed in a browser. The EHR client 118 is configured to transmit data to the EHR server 110 and retrieve data from the EHR server 110 for presentment to the clinician or other healthcare worker.

The client computing device 102 also includes a display 120, wherein an EHR graphical user interface (GUI) 122 (presented by way of the EHR client 118) is presented on the display 120. The EHR GUI 122 is configured to present EHR data 130 to a clinician or other healthcare worker, where the EHR data 130 is information about at least one patient. The EHR GUI 122 is further configured to receive information from the clinician or other healthcare worker about the at least one patient. A population health application GUI 131 can also be presented on the display 120, wherein the population health client 119, when executed by the processor 114, causes the population health GUI 131 to be displayed on the display 120. The population health GUI 131 depicts population health data 132. As will be described in greater detail below, this population health data 132 can indicate that a patient has been assigned to a patient population.

A plurality of external data systems 123 store patient data 124 that can be accessed by the second server computing device 105 by way of network connections. The external data systems 123 can be health information exchanges (HIEs), data maintained by other EHRs, or any other computer-readable data storage that stores data pertaining to patients. The second server computing device 105 can be configured to periodically access the external data systems 123, and the second server computing device 105 can store patient data 124 as population data 125. Additionally, the second server computing device 105 can be in communication with the first server computing device 104, and can include at least some of the patient data 127 in the population data 125. Accordingly, the population data 125 can include: 1) data about patients who are not serviced by the healthcare entity (where the ERR is employed): 2) data about patients who are serviced by the healthcare entity that is in the patient data 127; and 3) data about patients who are serviced by the healthcare entity that is not in the patient data 127. The population data 125 may be structured such that the population data 125 includes: 1) patient identifiers that uniquely (and anonymously) identify patients; and 2) data about such patients (e.g., demographic data, test results, etc.). The population data 125 can further include a mapping between identifiers in the patient data 127 and the aforementioned patient identifiers. Further, as will be described below, the population data 125 can include population labels that can be assigned to patient identifiers, where a population label assigned to a patient identifier indicates whether or not a patient (identified by the patient identifier) has been assigned to a patient population. A patient population can be, for instance, "diabetes", wherein an assignment of a label for such patient population indicates that a patient has conditions that correspond to other patients in the patient population.

Assigning Patient Population Labels to Patient Identifiers

The population health server 126, in general, is configured to analyze the population data 125 and determine, for each of a plurality of patient populations, whether each patient represented in the population data 125 is included in a patient population. The population health server 126 is further configured to execute queries pertaining to patient populations and return search results about the patient populations. There are numerous possible approaches for determining whether a patient is to be included in a patient population. A first exemplary approach is a rules-based approach (e.g., if data X, Y, and Z exists for the patient in the population data 125, the patient is to be assigned to patient population A). A second exemplary approach is clustering, where the population health server 126 can cluster patients with similar conditions together in a patient population. The population health server 126 can also employ artificial intelligence techniques to determine whether or not a patient should be labeled as belonging to a certain patient population. The population health server 126 can perform the above-described analysis as a background task, such that assignation of patients to patient populations can be periodically updated. In another example, the population health server 128 can perform such analysis as queries about patients are received.

Operation of the EHR and the Population Health Application in Conjunction

As indicated previously, the EHR and the population health application can operate in conjunction to present data to a healthcare worker (e.g., a clinician or care manager) that is operating the client computing device 102, where the data identifies that at least one patient has been assigned to at least one patient population by the population health server 126. There are three scenarios described herein: 1) when the population health server 126 assigns a patient to a patient population; 2) when a clinician is providing care to a patient; and 3) when a care manager is analyzing a patient population. These scenarios are discussed in turn.

Operation of the System 100 when a Patient is Added to a Patient Population

As described above, the population health server 126 can assign a label to a patient that indicates that the population health server 126 has determined that the patient belongs to a certain population. The definition of a population can be set forth by a standards board, by a healthcare enterprise, or other suitable entity. When the population health server 126 determines that a patient belongs to a patient population, the population health server 126 can construct a message for the population health client 119 and transmit the message to the client computing device 102 when the client computing device 102 executes the population health client 119 (and when the operator of the client computing device 102 is authorized to receive such message). In a non-limiting example, a clinician may cause the client computing device 102 to run the EHR client 118, and may provide authentication data to the EHR client 118 (e.g., username, password, biometric data, etc.). The EHR client 118 can cause the client computing device 102 to transmit the authentication data to the first server computing device 104, whereupon the server EHR 110 authenticates the clinician. The server EHR 110 can cause the server computing device 104 to transmit an authentication token to the client computing device 102, where it can be received and used by the EHR client 118 when communicating with the EHR server 102.

The EHR client 118 is in communication with the population health client 119, and can provide data to the population health client 119 that, for instance, is indicative of the identity of the clinician who has been authenticated by the EHR server 110. The population health client 119 can cause the client computing device 102 to transmit this data to the second server computing device 105, whereupon the population health server 126 searches for messages for the clinician. In this example, the population health server 126 determines that a patient of the clinician has been added to a certain patient population by the population health server 126 since the last time that the clinician used the population health client 119. The population health server 126 can cause the second server computing device 105 to transmit the above-described message to the client computing device 102 (for the population health client 119), and the population health client 119 can cause the population health GUI 131 to depict a notification. The notification can indicate that a patient of the clinician has been added to a patient population. For instance, the notification can be rendered on a badge, such that when the badge is selected, an identity of the patient and the population to which the patient has been assigned can be presented in the population health GUI 131. The population health GUI 131 can also depict recommended actions, wherein such actions can be to assist the clinician in removing any ambiguity as to whether or not the patient should be included in the patient population or assist the clinician in diagnosing the patient with a disease or other condition (as well as taking remedial action).

This system 100, in this scenario, has several advantages over conventional systems. For instance, the clinician (or care manager) can be notified when the patient is added to the population even if the patient has not been to the healthcare entity for care in quite some time. For instance, the patient may visit an orthopedic surgeon for removing meniscus around the knee, and may have bloodwork performed prior to surgery. Results from blood tests can be included in the patient data 124, and be retrieved by the second server computing device 105 and added to the population data 125. Based upon results of the blood tests (as well as other factors), the population health server 126 can place the patient in a patient population for diabetes. The clinician operating the client computing device 102 may be the primary care physician for the patient, and can be notified that the patient has been added to the diabetes patient population. The clinician can then initiate communication with the patient, thereby allowing remedial action to be undertaken much earlier when compared to what is possible with conventional computing systems.

Operation of the System 100 at the Point of Care

In an example, a clinician may be providing care to a patient (e.g., at a healthcare facility, through a video conference, etc.). The client computing device 102 is employed by the clinician, and the EHR has authenticated the clinician. The clinician, via the client computing device 102, sets forth data that identifies the patient to the EHR client 118. The EHR client 118, responsive to receiving the data that identifies the patient, causes the client computing device 102 to transmit a patient identifier for the patient to the first server computing device 104, where it is provided to the EHR server 110. The EHR server 110 searches the EHR data 127 using the patient identifier, and obtains search results. The EHR server 110 causes the first server computing device 104 to transmit a subset of the search results to the client computing device 102, and the EHR client 118 causes the search results to be included in the EHR data 130 shown in the EHR GUI 122 on the display 120.

The EHR client 118 provides the population health client 119 with the patient identifier, and the population health client 119 causes the client computing device 102 to transmit the patient identifier to the second server computing device 105. The population health server 126 receives the patient identifier and searches over the population data 125 based upon the patient identifier, and obtains search results. The search results can include an indication that the patient belongs to one or more patient populations. The population health server 126 causes the server computing device 105 to transmit the search results to the client computing device 102. The population health client 119 causes an indication to be presented in the population health data 132 in the population health GUI 131 (shown on the display 120 simultaneously with the EHR GUI 122), where the indication notifies the clinician that the patient has been assigned to the one or more patient populations by the population health application (where the patient population is one that is monitored by the clinician). Again, this is advantageous over conventional computing systems, which are unable to close gaps in care that result from patients being provided with care by several different medical professionals.

Operation of the System 100 when a Care Manager is Analyzing a Patient Population A care manager at a healthcare entity may be tasked with monitoring treatment of a large number of patients, to ensure that such patients are being proactive with respect to one or more health conditions. For instance, a care manager may be tasked with contacting patients at the healthcare facility who are diagnosed with diabetes or who may be diabetic, such that a visit with a clinician can be scheduled. The system 100 can provide the care manager with a list of patients of the healthcare entity who have been assigned to the diabetes population by the population health application.

In an example, the client computing device 102 can receive authentication credentials from the care manager by way of the EHR client 118, and the EHR client 118 can cause the client computing device 102 to transmit the authentication credentials to the first server computing device 104. The EHR server 110 authenticates the care manager based upon the authentication credentials, and causes the first server computing device 104 to transmit authentication data (e.g., an authentication token) to the client computing device 102, where it is provided to the EHR client 118.

The EHR client 118 can further obtain patient identifiers from the EHR server 110, where the patient identifiers are for patients monitored by care manager. The EHR client 118 can provide the patient identifiers to the population health client 119. Additionally or alternatively, the EHR client 118 can provide data that identifies the care manager to the population health client 119. The care manager can set forth a query to the population health client 119, where the query indicates that the care manager wishes to be provided with all patients managed by the care manager who have been assigned to the diabetes population by the population health application. The population health client 119, in response to receiving the query, causes the client computing device 102 to transmit the query to the population health server 126. For instance, the query can include the list of patients being managed by the care manager and an identity of the patient population (diabetes). The population health server 126 searches the population health data based upon the query, and returns a subset of the patients to the population health client 119, wherein each patient in the subset of patients has been assigned to the diabetes patient population by the patient population application. The population health client 119 can, in response to receiving the subset of the patients, present the subset of patients in the population health GUI 131. The care manager can then click through each patient in the subset of patients, obtain appropriate contact information, and contact the patients. Further, the population health client 119 and/or population health server 126 can organize the patients in the subset of patients in any suitable manner, such as by time of most recent visit.

Again, the computing system 100 is advantageous over conventional computing systems, as the computing system 100 reduces gaps in care. The population health server 119 assigns patients to patient populations based upon, for instance, data received from various different data sources (e.g., which may be associated with different, non-cooperating medical practices). Hence, for example, gaps in care between an oncologist, a primary care physician, and an allergist can be closed.

Figure 2:
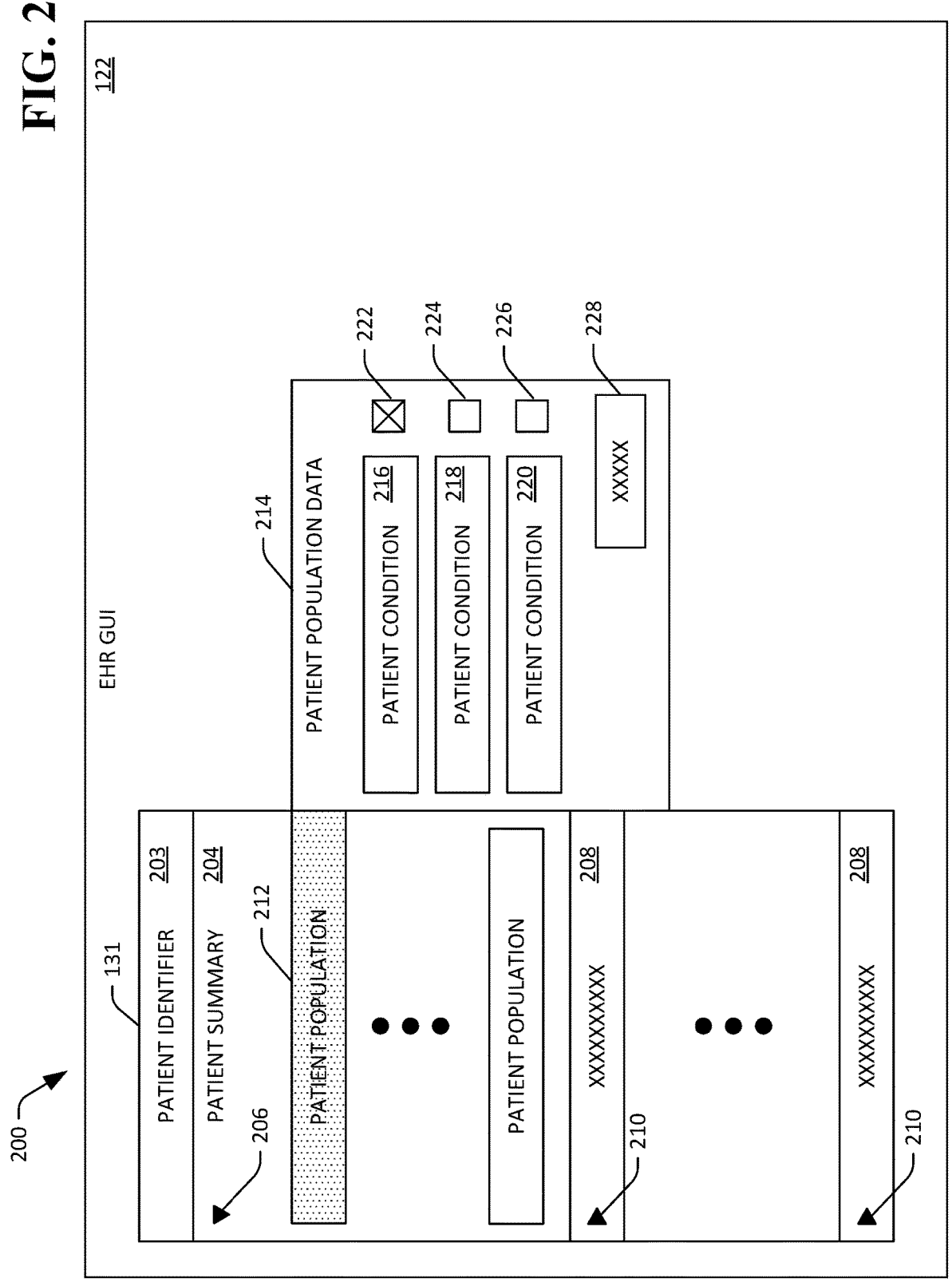
FIG. 2 is a schematic of an exemplary graphical user interface.

Referring now to FIG. 2, an exemplary depiction of the EHR GUI 120 and the population health GUI 131 is illustrated. While the population health GUI 131 is depicted as being displayed over the EHR GUI 120, it is to be understood that the population health GUI 131 can be displayed as a portion of the EHR GUI 120. The population health GUI 131 includes a patient identifier 203, which can identify a patient who is being provided care by the clinician. For example, the patient identifier 203 can be or include a name of the patient, an image of the patient, or other information pertaining to the identity of the patient. The population health GUI 131 may also include a patient summary 204 that sets forth various information about the patient. For example, the patient summary 204 can include information such as a discharge date, a date of a follow-up appointment, a number of visits by the patient to a healthcare facility, etc. The patient summary 204 can be collapsed or expanded responsive to receiving a selection of an interactive graphical element 206. Similarly, in population health GUI 131, additional graphical elements 208 pertaining to specific information about a patient (e.g., diagnoses, medications, allergies, etc.) can be collapsed or expanded via selection of respective interactive graphic elements 210.

The patient summary 204 also includes a graphical element 212 indicative of a patient population to which the patient referred to by the patient identifier 203 belongs. Responsive to selection of the patient population element 212, the element 212 can be highlighted and a patient population data pane 214 can be displayed. The patient population data pane 214 comprises a plurality of graphical elements 216-220 that are indicative of patient conditions. The patient conditions are conditions about the patient that support inclusion of the patient in the patient population of which the graphical element 212 is indicative. For example, if the patient population is patients having a risk for heart disease, a first patient condition represented by the graphical element 216 can be high cholesterol, a second patient condition represented by the graphical element 218 can be high blood pressure, and a third patient condition represented by the graphical element 220 can be obesity. It is to be understood that a number of graphical elements corresponding to patient conditions that is shown in the patient population data pane 214 can vary based upon the patient and the population. By way of example, for a different patient having a risk of heart disease, there may be only two patient conditions supporting a classification of the patient into the population of patients having a risk of heart disease. Thus, for the different patient only two graphical elements indicative of patient conditions may be displayed in the patient population data pane 214. Likewise, for a same patient or a different patient, a different population may have a different number of corresponding patient conditions.

The population health GUI 131 can also have interactive graphical elements 222-226 corresponding to the patient condition elements 216-220, respectively. The interactive graphical elements can be used in connection with taking some action with respect to the patient conditions identified by the patient condition elements 216-220. For example, responsive to receiving a selection of one or more of the interactive graphical elements 222-226 and a subsequent selection of a button 228, the client computing device 102 can transmit data to the server computing device 104 and/or the server computing device 105 (e.g., by way of the EHR client 118 or the population health client 119) that causes the server computing device 104 to take action relative to the patient conditions associated with the one or more selected interactive graphical elements. In one example, the data elements 216-220 can each represent a task that is performable by the clinician and/or patient that can disambiguate whether the patient should be included in the patient population (e.g., an overdue blood test, an overdue physical, an indication that the patient has never had a particular examination, etc.). In the one example, when the interactive element 222 is selected and a selection of the button 228 is received, the client computing device 102 can transmit data to the server computing device 104 indicating an order to schedule a test or other appointment relative to the condition corresponding to the graphical element 216. In another example, when the client computing device 102 receives a selection of the button 228, the client computing device 102 can transmit data to the server computing device 105 that causes the server computing device 105 to modify the population data 128 to indicate that the patient does not belong in the patient population. Thus, the population health GUI 131 can be used in connection with allowing a clinician to modify and override assignments of patients to patient populations by the population health application. Furthermore, responsive to such a modification, the population health GUI 131 can be modified to reflect that the patient is no longer a part of the population. For example, responsive to a clinician indicating that a patient does not belong in the population corresponding to the graphical element 212, the graphical element 212 can be removed from the population health GUI 131.

Figure 3:
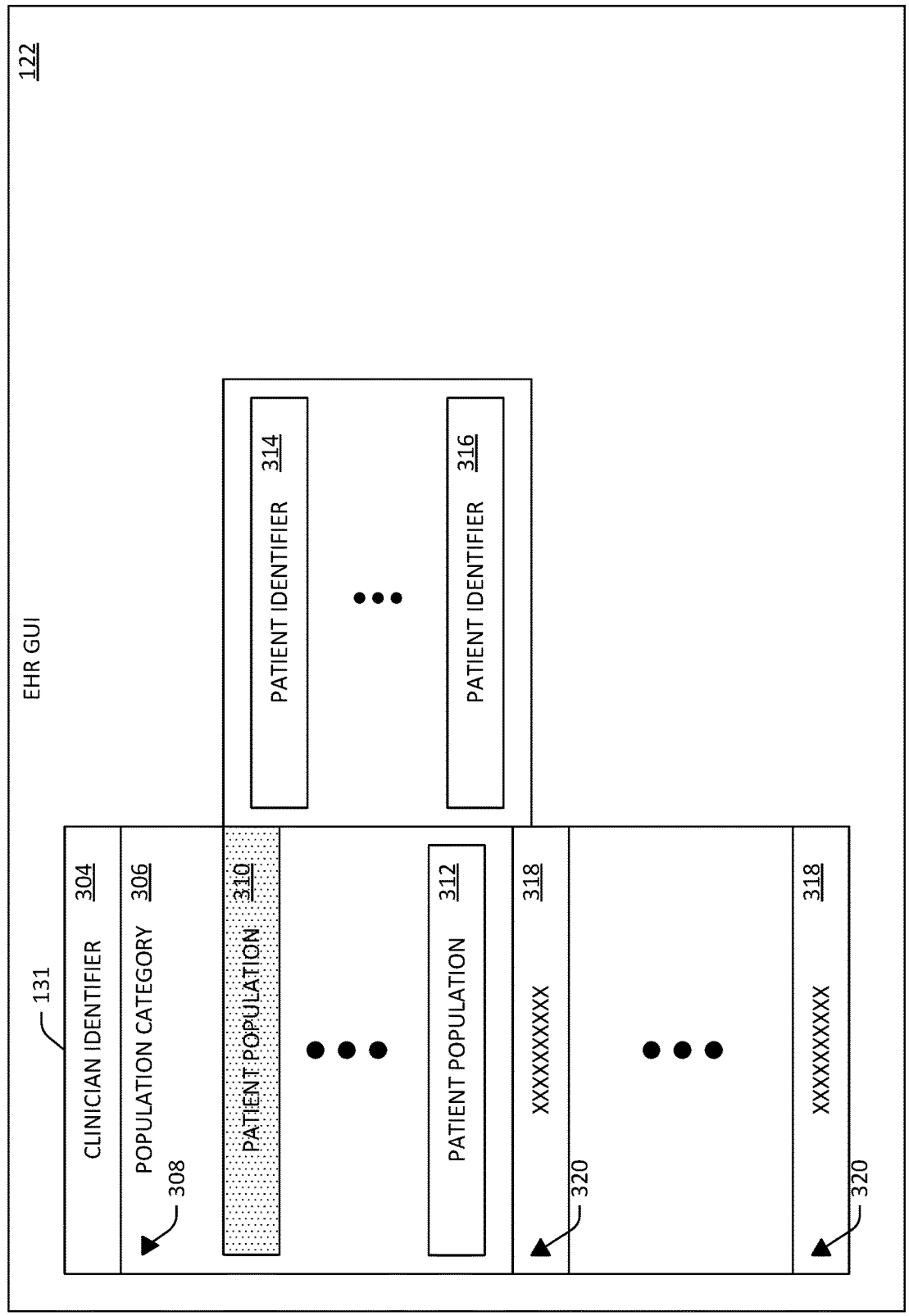
FIG. 3 is a schematic of a second exemplary graphical user interface.

Referring now to FIG. 3, another exemplary depiction of the EHR GUI 122 and the population health GUI 131 shown concurrently on the display 120 of the client computing device 102 is illustrated. While the population health GUI 131 is depicted as being displayed over the EHR GUI 122, it is to be understood that the population health GUI 131 can be displayed as a portion of the EHR GUI 122. The population health GUI 131 comprises a clinician identifier 304 that identifies a clinician user of the client computing device 102. The clinician identifier 304 can be or include a name of the clinician, an image of the clinician, or other information pertaining to the identity of the clinician. The overlay 302 further comprises a population category portion 306 that can be expanded or collapsed based upon a selection of a drop-down arrow 308. The population category portion 306 corresponds to a patient population category, and the population category portion 306 further comprises one or more portions 310 and 312 indicative of patient populations in the patient population category. By way of an example, the patient population category can be "Gaps in Care." In the example, the population corresponding to the first patient population portion 310 can be a first type of gap in care (e.g., missed appointments) and the population corresponding to the second patient population portion 312 can be a second type of gap in care (e.g., non-scheduled follow-ups).

Responsive to receiving a selection of the first patient population portion 310, the client computing device 102 can cause a plurality of patient identifiers 314-316 to be displayed. The patient identifiers 314-316 refer to and identify patients belonging to the population of the selected patient population portion 310. Via selection of one of the patient population portions 310-312, a clinician user can see at a glance which of her patients have, for example, various gaps in care, a risk for a particular health condition, a characteristic of interest, etc. The population health GUI 131 therefore allows the clinician user to more efficiently identify patients that may need to be prioritized for attention by the clinician rather than requiring the clinician to manually examine patient health records for dozens, or perhaps hundreds, of patients in order to identify these patients of interest. Responsive to receiving a selection of one of the patient identifiers 314-316, the client computing device 102 can display a portion of a patient health record associated with the patient, or take other action with respect to the patient. In another example, responsive to receiving a selection of one of the patient identifiers 314-316 in the population health GUI 131, the client computing device 102 can update the population health GUI such that it has additional information pertaining to the patient identified by the selected identifier. The population health GUI 131 can include additional graphical elements 318 that are expandable responsive to receipt of a selection of interactive graphical elements 320.

Figure 4:
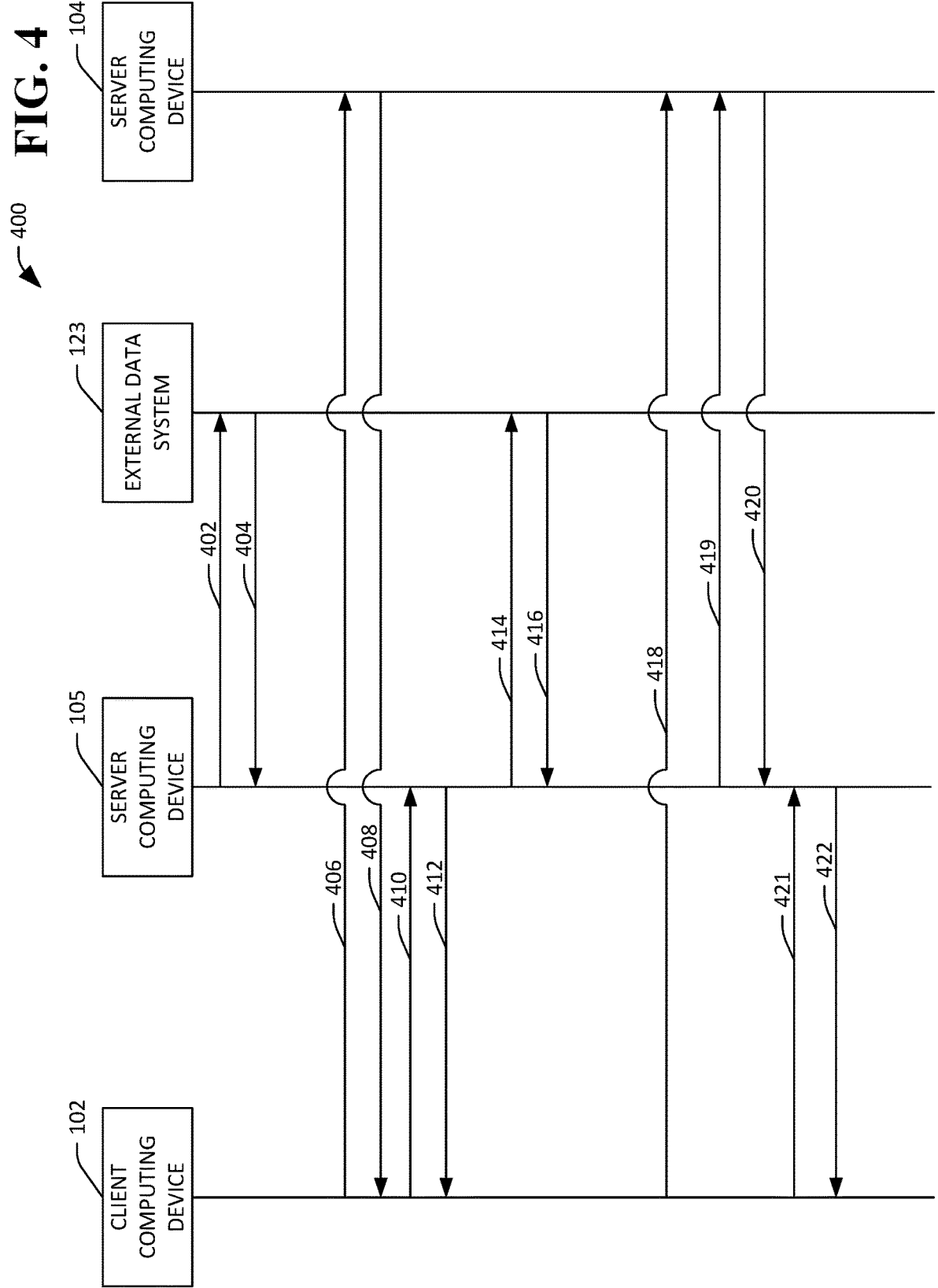
FIG. 4 illustrates a communications diagram.

Referring now to FIG. 4, an exemplary communications diagram 400 is illustrated. At 402, the second server computing device 105 transmits a request to an external data system 123 for health data (e.g., some of which may pertain to patients who have electronic health records maintained by the EHR). The second server computing device 105 then receives the patient data from the external data system 123 at 404, whereupon it is retained in the population data 125. Further, the population data 125 can include data maintained by the EHR server 110.

At 406, the client computing device 102 transmits authentication data set forth by a clinician or other healthcare worker to the first server computing device 104, wherein the EHR server 110 executing on the first server computing device 104 authenticates the clinician or other healthcare worker based upon the authentication data. At 408, the EHR server 110 may cause data, customized for the clinician or other healthcare worker, to be transmitted for display in the EHR GUI 122 on the display 120 of the client computing device 102. The data transmitted at 408 can, for example, cause the client computing device 102 to display a GUI comprising a list of the clinician's patients. At 410 the client computing device 102, responsive to receiving an indication of a patient via an input interface of the client computing device 102, transmits data indicative of the patient to the server computing device 105. The server computing device 105, at 412, transmits data indicative of one or more populations to which the indicated patient belongs to the client computing device 102.

At 414 the server computing device 105 can again transmit a request to the external data system 123 for any new data pertaining to patients having patient health records associated with the EHR 110. The external data system 123 provides the new data to the server computing device 105 at 416, whereupon the server computing device 105 can update the population data 125 with the new data. At 418 the client computing device 102 provides the server computing device 104 with data pertaining to a patient having a health record associated with the EHR. The data can reflect information input by a clinician at the client computing device 102 relative to a patient's vital signs, an outcome of an examination of the patient, a diagnosis of a health condition of the patient, etc. At 419, the server computing device 105 can issue a query to the first server computing device 104, the query being a request for data pertaining to patient health records. At 420, the first server computing device 104 provides data to the server computing device 105 that comprises patient health records updated by the server computing device 104 responsive to receiving the data at 418.

The server computing device 105 can update the population data 128 based upon the data received from the external data system 123 at 416 and the data received from first server computing device at 420. For example, based upon the data received by the second server computing device 105 from the external data system 123 or the first server computing device 104 at 416 and 420, respectively, the population health server 126 can identify that a patient had an examination or other appointment. If the patient had previously been assigned to a population of patients as a function of a lack of data pertaining to a certain condition (e.g., lack of a blood test) that would be acquired at the appointment, the second server computing device 105 can update population data pertaining to the patient and the patient list to reflect that the patient has had the appointment.

At 421, the client computing device 102 provides the second server computing device 105 with a request indicative of an identity of a clinician user of the client computing device 102 or a patient health record associated with the EHR. Responsive to receiving the request from the client computing device 102 at 421, the server computing device 105 can transmit data to the client computing device 102 at 422 that is configured to cause the client computing device 102 to display a GUI comprising patient population data. For example, the GUI can comprise a list of patients assigned to a population by the population health server 126, wherein one or more patients has been added to or removed from the list based upon the data received by the second server computing device 105 at 416 or 420. In another example, the GUI can comprise an indication of populations assigned to a patient health record, wherein one or more of the populations was assigned to the patient health record based upon the data received by the second server computing device 105 at 416 or 420.

Figure 5:
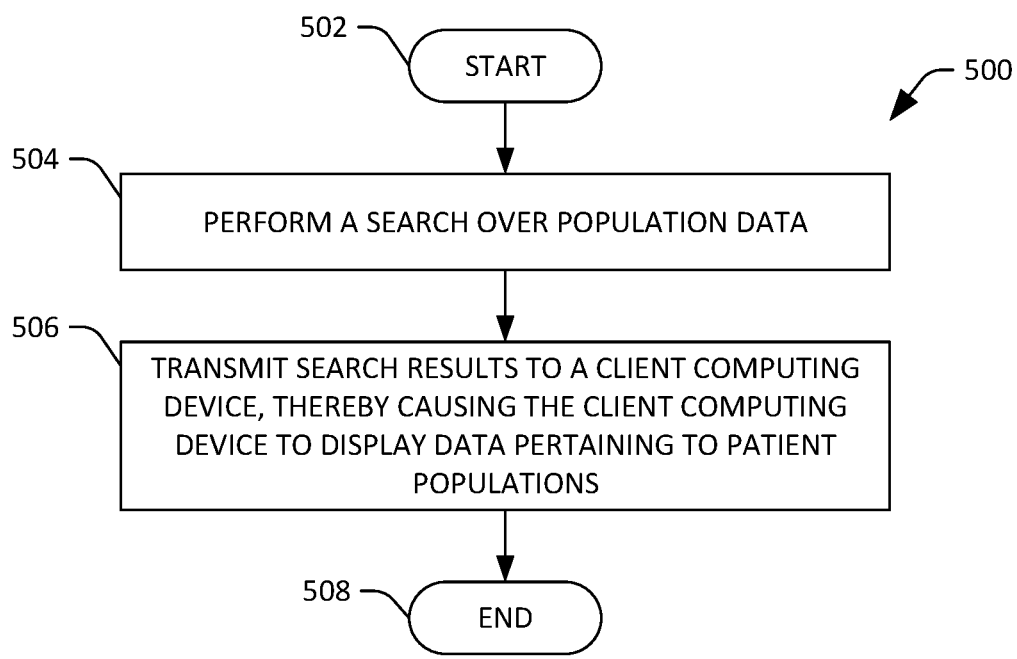
FIG. 5 is a flow diagram that illustrates an exemplary methodology for displaying population data pertaining to patients of a clinician.

FIG. 5 illustrates an exemplary methodology 500 relating to presenting to clinicians population information pertaining to the clinicians' patients. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodology can be stored in a computer-readable medium, displayed on a display device, and/or the like.

Referring now to FIG. 5, a methodology 500 executed by a server computing device that facilitates discovery and presentation of patient population information is illustrated. The methodology 500 begins at 502, and at 504 a search is performed over population data, wherein the population data includes data that identifies patients and corresponding labels that identify patient populations to which one or more of the patients belong. Performing of the search results in identification of at least one patient and a patient population to which the patient has been assigned. At 506, the search results are transmitted to a client computing device, wherein the client computing device executes a population health client and an EHR client. Provision of the search results causes the client computing device to display data relating to patient populations on a display. The methodology 500 completes at 508.

Figure 6:
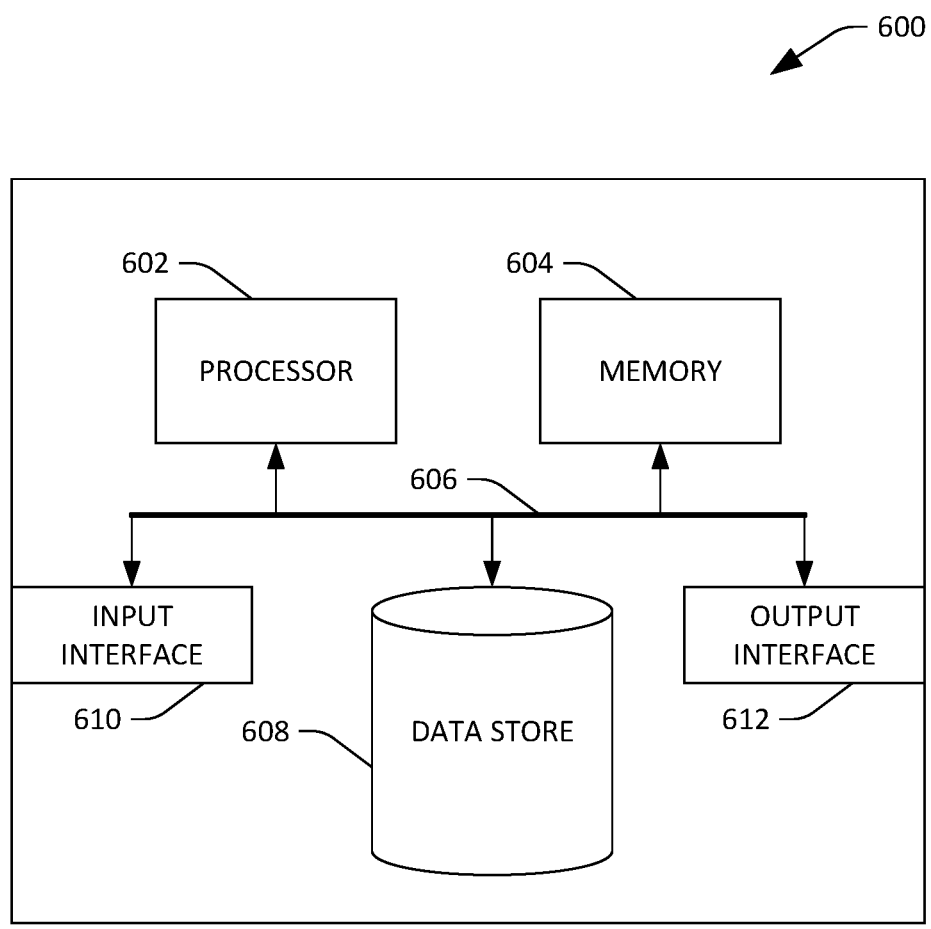
FIG. 6 is a schematic of an exemplary computing system.

Referring now to FIG. 6, a high-level illustration of an exemplary computing device 600 that can be used in accordance with the systems and methodologies disclosed herein is illustrated. For instance, the computing device 600 may execute an EHR server and/or EHR client. By way of another example, the computing device 600 can execute a patient population client and/or patient population server. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store patient health records, patient population data, etc.

The computing device 600 additionally includes a data store 608 that is accessible by the processor 602 by way of the system bus 606. The data store 608 may include executable instructions, patient health records, community health records, patient population data, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system comprising a server computing device that executes a population health server application, the server computing device configured to perform acts comprising:
   receiving a query from a population health client application executing on a client computing device, the client computing device in communication with the server computing device and a second server computing device that executes a server electronic health record application (EHR), the query comprising a patient identifier received by the population health client application from a client EHR executing on the client computing device, the patient identifier indicative of a patient, the patient identifier being received by the population health client application from the client EHR based upon data pertaining to the patient being displayed in a graphical user interface (GUI) of the client EHR, the data pertaining to the patient being received by the client EHR from the server EHR;
   performing a search over population data based on the query, the population data comprising data pertaining to a plurality of patients sourced from at least one data source other than the server EHR, the search based upon the query, wherein search results obtained from the search comprise:
      an indication that the patient belongs to a patient population, the indication based upon data pertaining to the patient that is included in the population data; and
      an indication of a patient condition pertaining to the patient, wherein the patient condition is a condition that supports inclusion of the patient in the patient population;
   causing the client computing device to display graphical data within a GUI of the client EHR or within a GUI of the population health client application that is displayed contemporaneously with the GUI of the client EHR, the graphical data based upon the search results, wherein the graphical data indicates to an operator of the client computing device that the patient belongs to the patient population, the graphical data further including a selectable element; and
   receiving a communication from the population health client responsive to the selectable element being selected at the client computing device, wherein responsive to receiving the communication, the population health server application updates the population data to indicate that the patient does not belong to the patient population.

2. The system of claim 1, the acts further comprising:
   receiving a second query from the population health client application;
   performing a second search based upon the second query to generate second search results, wherein the second search results obtained from the second search comprise:
      identities of a plurality of patients; and
      an indication that each patient in the plurality of patients belongs to the patient population, wherein the graphical data indicates to the operator of the client computing device that each patient in the plurality of patients belongs to the patient population; and
   causing the client computing device to display second graphical data within the GUI of the client EHR or within the GUI of the population health client application, the second graphical data indicates that patients in the plurality of patients belong to the patient population.

3. The system of claim 1, wherein the graphical data is presented in the GUI for the population health client application.

4. The system of claim 1, the acts further comprising:
   updating the patient population data to indicate that the patient belongs to the patient population prior to the query data being received from the client computing device.

5. The system of claim 4, wherein the patient is assigned to the patient population based upon data received at the server computing device from a plurality of different data sources.

6. The system of claim 2, wherein the second query comprises
   an identifier of an operator of the client computing device, and wherein the plurality of patients are patients indicated in the population health data as being assigned to the operator of the client computing device.

7. A method executed by a first server computing device that is in communication with a client computing device, the client computing device executes an electronic health record (EHR) client and a patient population client, the method comprising:
   receiving data query from the patient population client executing on the client computing device, the query comprising a patient identifier received by the patient population client from the EHR client, the patient identifier indicative of a patient, the patient identifier being received by the patient population client based upon health data pertaining to the patient being displayed in a graphical user interface (GUI) of the EHR client, the health data being received by the EHR client from an EHR server executing on a second server computing device;
   performing a search over population data, the search based upon the query, the population data comprising data pertaining to a plurality of patients that is sourced from at least one data source other than the EHR server, and wherein search results obtained from the search comprise:

an indication that the patient belongs to a patient population, the indication based upon data pertaining to the patient that is included in the population data; and an indication of a patient condition pertaining to the patient, wherein the patient condition is a condition that supports inclusion of the patient in the patient population;

causing the client computing device to display graphical data based upon the search results, wherein the graphical data indicates to an operator of the client computing device that the patient belongs to the patient population, the graphical data displayed within the GUI of the EHR client or within a GUI of the patient population client that is displayed contemporaneously with the GUI of the EHR client at the client computing device, wherein the graphical data further includes a selectable element; and updating the population data to indicate that the patient does not belong to the patient population responsive to receiving a communication from the patient population client, the communication transmitted by the population client responsive to the selectable element being selected at the client computing device.

8. The method of claim 7, further comprising:
receiving a second query from the patient population client;
performing a second search over the population data based upon the second query to generate second search results, wherein the second search results obtained from the second search comprise:
identities of a plurality of patients; and
an indication that each patient in the plurality of patients belongs to the patient population, wherein the graphical data indicates to the operator of the client computing device that each patient in the plurality of patients belongs to the patient population; and
causing the client computing device to display second graphical data within the GUI of the EHR client or within the GUI of the patient population client, the second graphical data indicates that patients in the plurality of patients belong to the patient population.

9. The method of claim 7, wherein the graphical data is presented in the GUI of the patient population client.

10. The method of claim 7, the acts further comprising:
updating the population data to indicate that the patient belongs to the patient population prior to the query being received from the client computing device.

11. The system of claim 10, wherein the population data is updated based upon data received at the server computing device from a plurality of different data sources.

12. The method of claim 8, wherein the second query comprises
an identifier of an operator of the client computing device.

13. A nontransitory computer-readable storage medium comprising instructions that, when executed by at least one processor, cause the at least one processor to perform acts comprising:
responsive to receiving a query from a population health client executing on a client computing device, the query being comprising a patient identifier received by the population health client from a client electronic health records application (EHR) executing on the client computing device, the patient identifier indicative of a patient and received by the population health client from the client EHR based upon health data pertaining to the patient being displayed in a graphical user interface (GUI) of the client EHR, the health data being data received by the client EHR from a server EHR executing on a server computing device, performing a search over population data based upon the query, the population data comprising data pertaining to a plurality of patients sourced from at least one data source other than the server EHR, the search based upon the query, wherein search results obtained from the search comprise:
an indication that the patient belongs to a patient population; and
an indication of a patient condition pertaining to the patient, wherein the patient condition is a condition that supports inclusion of the patient in the patient population;
causing the client computing device to display graphical data based upon the search results, wherein the graphical data indicates to an operator of the client computing device that the patient belongs to the patient population, and wherein the graphical data is displayed within a GUI of the client EHR or within a GUI of the population health client that is displayed simultaneously with the GUI of the client EHR at the client computing device, the graphical data further including a selectable element; and
responsive to receiving a communication from the population health client, the communication received responsive to the selectable element being selected at the client computing device, updating the population data to indicate that the patient does not belong to the patient population.

14. The nontransitory computer-readable storage medium of claim 13, the acts further comprising:
receiving a second query from the population health client;
performing a second search based upon the second query to generate second search results, wherein the second search results obtained from the second search comprise:
identities of a plurality of patients; and
an indication that each patient in the plurality of patients belongs to the patient population, wherein the graphical data indicates to the operator of the client computing device that each patient in the plurality of patients belongs to the patient population; and
causing the client computing device to display second graphical data within the GUI of the client EHR or within the GUI of the population health client, the second graphical data indicates that patient in the plurality of patients belong to the patient population.

15. The nontransitory computer-readable storage medium of claim 13, wherein the graphical data is presented in the GUI for the population health client.

16. The nontransitory computer-readable storage medium of claim 13, the acts further comprising:
assigning the patient to the patient population prior to the query data being received from the client computing device.

17. The nontransitory computer-readable storage medium of claim 16, wherein the patient is assigned to the patient population based upon data received at the server computing device from a plurality of different data sources.

18. The system of claim 2, wherein the second query comprises data indicative of the patient population.

19. The system of claim 4, wherein the updating the population data prior to the query being received is based upon the patient condition of the patient being indicated in the population data.

* * * * *